(12) United States Patent
Hanby

(10) Patent No.: US 9,802,183 B2
(45) Date of Patent: Oct. 31, 2017

(54) DIFFUSION/CHEMICAL REACTION/SPECTROMETRIC DEVICE FOR THE ANALYSIS OF PETROLEUM HYDROCARBONS IN ENVIRONMENTAL AND GEOLOGICAL FORMATION SAMPLES

(75) Inventor: John David Hanby, Katy, TX (US)

(73) Assignee: Charles D. Fator, Houston, TX (US)

( * ) Notice: Subject to any disclaimer, the term of this patent is extended or adjusted under 35 U.S.C. 154(b) by 314 days.

(21) Appl. No.: 13/352,629

(22) Filed: Jan. 18, 2012

(65) Prior Publication Data

US 2013/0183767 A1 Jul. 18, 2013

(51) Int. Cl.
*B01J 31/06* (2006.01)
*B01J 31/02* (2006.01)
*G01N 33/18* (2006.01)
*G01N 33/24* (2006.01)
*G01N 1/40* (2006.01)

(52) U.S. Cl.
CPC .......... *B01J 31/06* (2013.01); *B01J 31/0231* (2013.01); *G01N 33/1833* (2013.01); *G01N 33/241* (2013.01); *B01J 2231/4205* (2013.01); *G01N 2001/4061* (2013.01); *Y10T 436/255* (2015.01)

(58) Field of Classification Search
CPC ............................... G01N 33/00; G01N 30/74
USPC ......... 422/63, 78, 82.05; 436/164, 171, 178; 502/159
See application file for complete search history.

(56) References Cited

U.S. PATENT DOCUMENTS

| 4,992,379 | A | 2/1991 | Hanby |
| 5,020,910 | A * | 6/1991 | Dunn ..................... G01J 3/0259 356/328 |
| 5,686,724 | A | 11/1997 | Spilker et al. |
| 5,834,655 | A | 11/1998 | Lad et al. |
| 6,040,191 | A * | 3/2000 | Grow ............................. 506/12 |
| 6,444,461 | B1 * | 9/2002 | Knapp et al. .............. 435/283.1 |
| 7,518,710 | B2 * | 4/2009 | Gao et al. ........................ 356/73 |
| 2003/0082820 | A1 * | 5/2003 | Perbost ................ B01J 19/0046 506/7 |
| 2004/0121402 | A1 * | 6/2004 | Harper et al. ................. 435/7.1 |

FOREIGN PATENT DOCUMENTS

| JP | 2005164402 A | 6/2005 |
| WO | WO 9707393 A1 * | 2/1997 |

OTHER PUBLICATIONS

PCT/US2013/022263 International Search Report and Written Opinion dated May 15, 2013 (10 p.).
Srirattnai, Kusoomjin, et al., "Encapsulated AlCl3: A Convenient Catalyst for the Alkylation of Benzene with Dodecene," Tetrahedron Letters 43 (2002), 4555-4557, Elsevier Science, Ltd. (3 p.).

* cited by examiner

Primary Examiner — Lyle Alexander
Assistant Examiner — Bryan Kilpatrick
(74) Attorney, Agent, or Firm — Conley Rose, P.C.

(57) ABSTRACT

An analytical device configured for the introduction of the liquid or solid sample into a sample chamber where it is extracted by a chlorinated hydrocarbon solvent, wherein the extract then passes into a chamber where it undergoes a Friedel-Crafts (FC) reaction.

17 Claims, 4 Drawing Sheets

Figure 1:
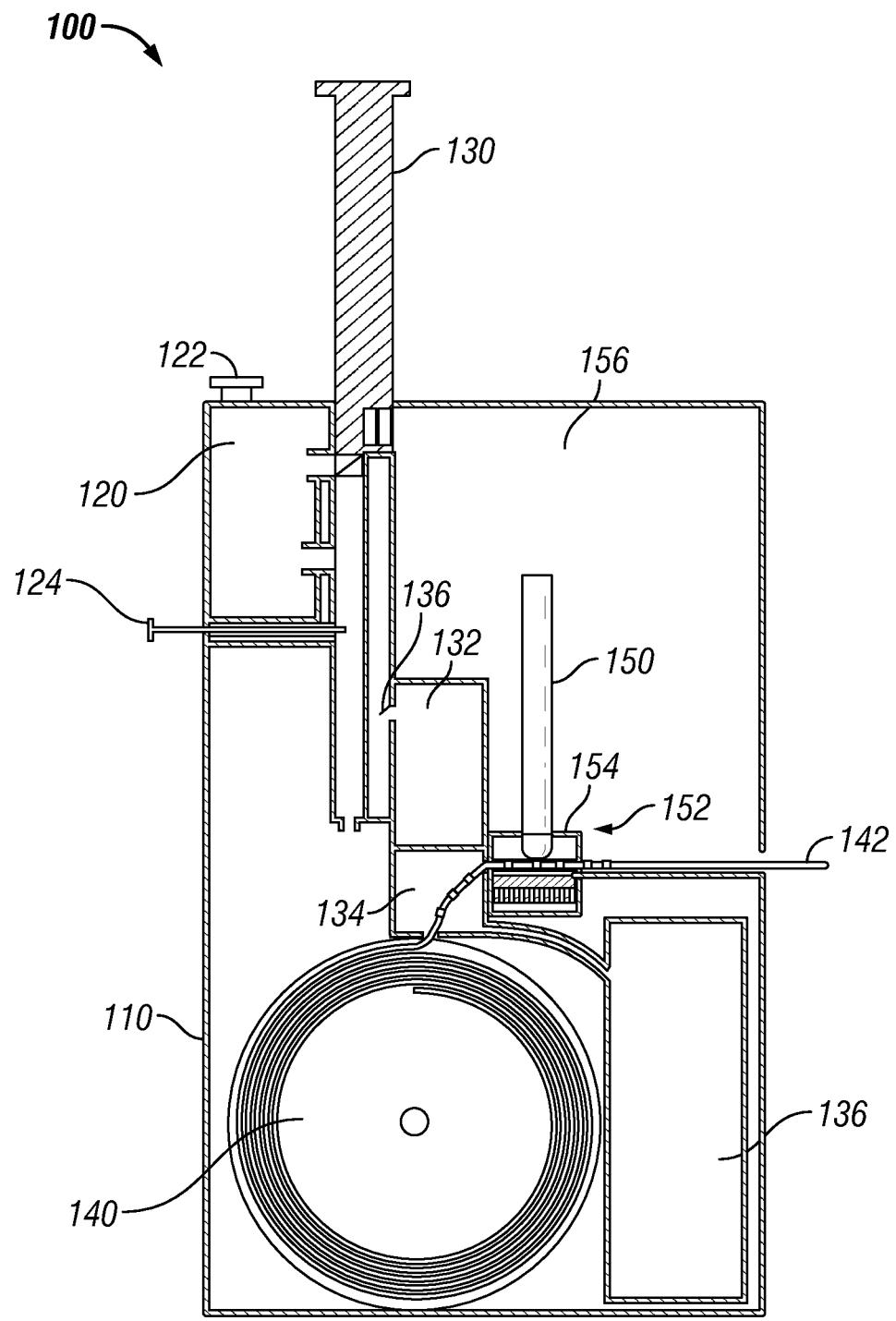

DIFFUSION/CHEMICAL REACTION/SPECTROMETRIC DEVICE FOR THE ANALYSIS OF PETROLEUM HYDROCARBONS IN ENVIRONMENTAL AND GEOLOGICAL FORMATION SAMPLES

BACKGROUND

The present invention relates generally to the analysis of hydrocarbons in environmental or geological samples.

Chromophores in the ultraviolet and visible regions of the electromagnetic spectrum are produced by Friedel-Crafts reactions (FCR) with a wide variety of the chemical constituents in crude oil and crude oil fractions. These chromophores serve as spectral markers which fingerprint a petroleum substance allowing for identification of the type and/or the source of the substance. This fingerprinting of petroleum substances may provide information for environmental investigation and assessment. It also serves as extremely valuable information in the Oil & Gas Exploration and Production (E&P) industry in the search for, and efficient production of, petroleum. Field kits for environmental testing of hydrocarbons based on U.S. Pat. No. 4,992,379 by the present inventor have been utilized in the industry. However, they lack the capacity for immediate or on-site read-out of the chromophoric signals produced by these kits.

SUMMARY

Disclosed herein is an analytical device that provides chemical composition spectrometric data on surface and sub-surface samples is disclosed herein. The device provides for the introduction of the liquid or solid sample into a sample chamber where it is extracted by a chlorinated hydrocarbon solvent. The extract then passes into a chamber where it undergoes Friedel-Crafts reactions (FCR), catalyzed by a polymer-encased Lewis acid, which is one segment of a chain of packets of this same catalyst. This FC reaction produces characteristic colors, which provide specific quantitative and qualitative chemical information about the hydrocarbon substance, e.g. fuel, solvent, crude oil, etc. being analyzed. The polymer-encased chain of packets then passes into a module containing a spectrometer consisting of a tungsten/halogen light source, a diffraction grating, and a CCD-based detector that reads the spectral information and sends the digital information to a microprocessor such as a computer.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

DESCRIPTION OF THE (3) DRAWINGS

Figure 2:
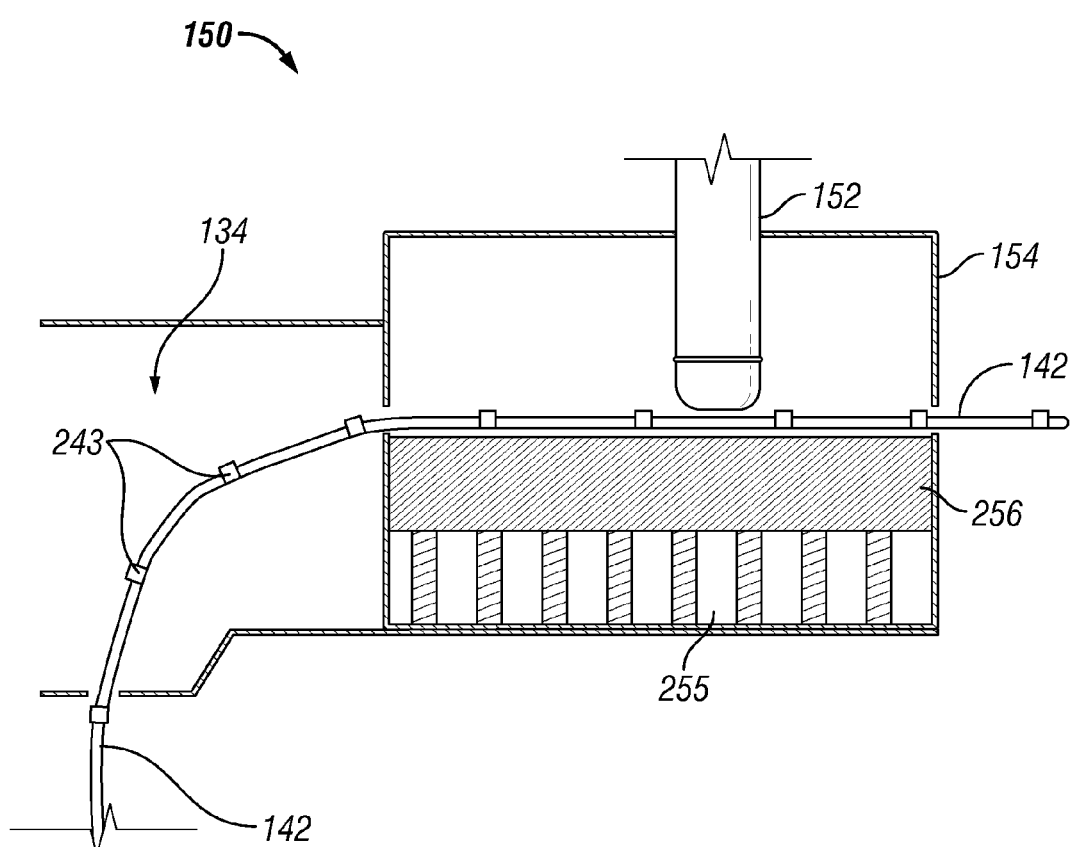
Figure 3:
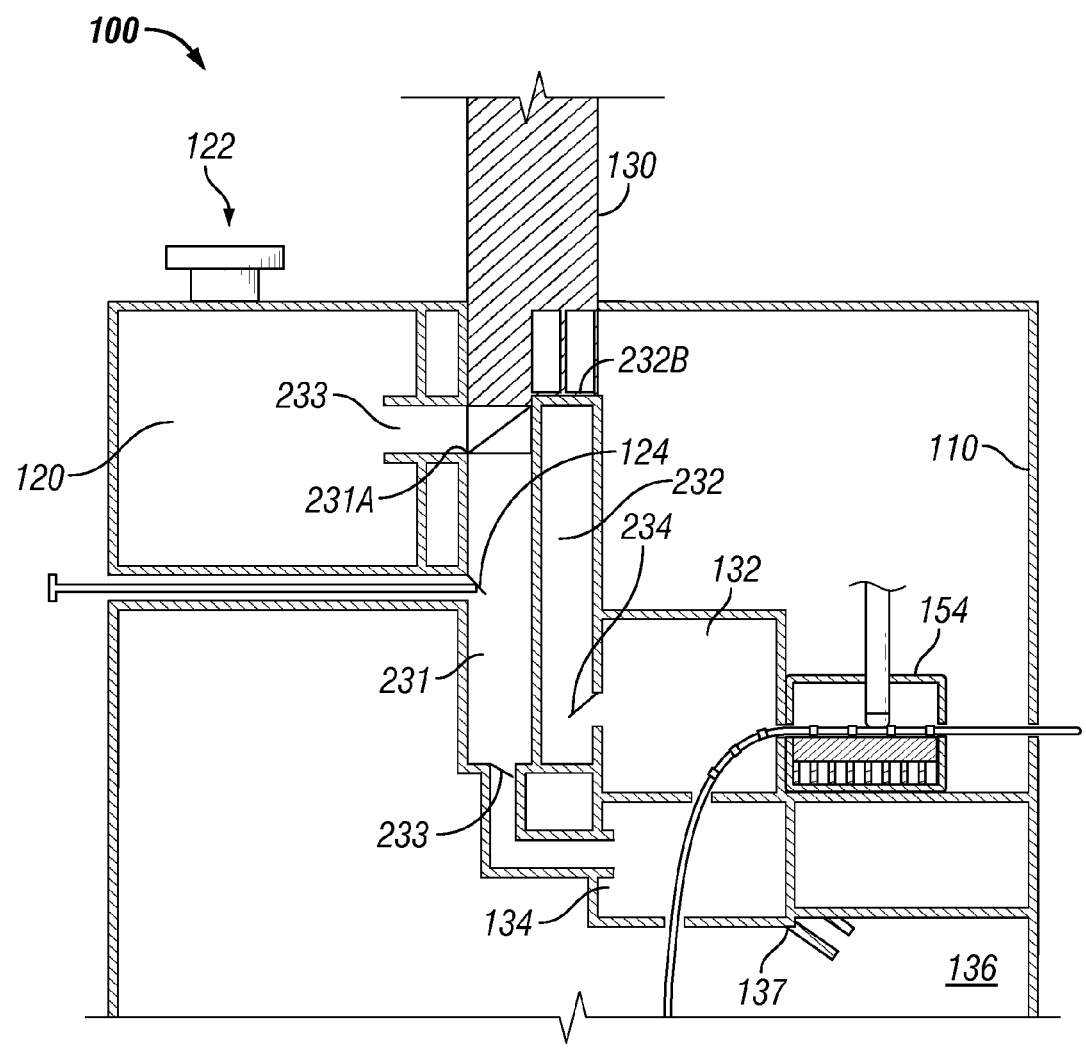

For a detailed description of various embodiments of the invention, reference will now be made to the accompanying drawings in which:

FIG. 1 illustrates a device for the extraction, chemical-reaction (colorimetric), and spectrometric analysis according to one embodiment of the present disclosure FIG. 2 illustrates a device comprising optical components of the CCD spectrometer according to one embodiment of the present disclosure FIG. 3 illustrates a device comprising a valving arrangement according to one embodiment of the present disclosure.

Figure 4:
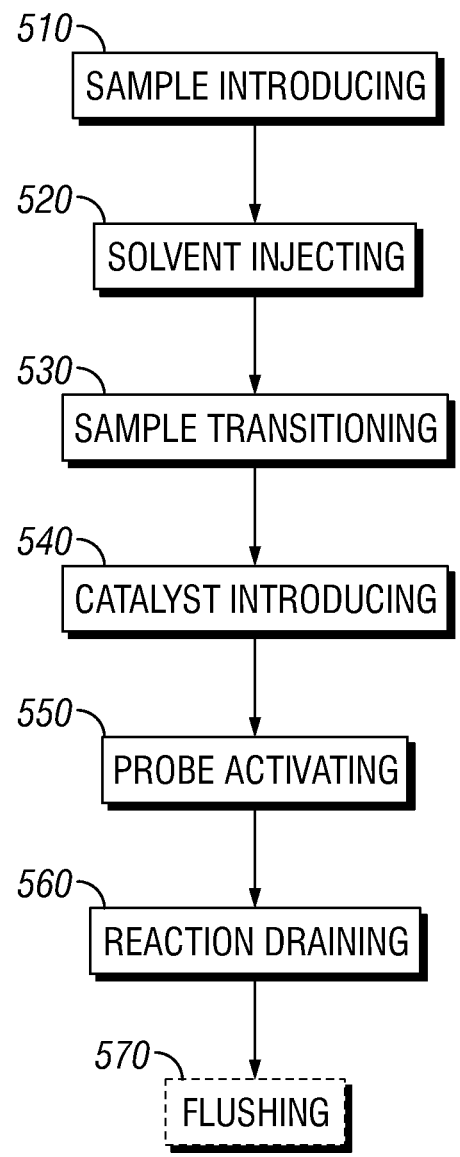

FIG. 4 illustrates a method for chromographic analysis according to one embodiment of the present disclosure.

DETAILED DESCRIPTION

The present disclosure has two (2) application configurations described herein. In one configuration, there is described a hand-held device for transport to the field for soil or water analysis. In another configuration the device may be transported downhole as part of a wireline tool. Without limitation, in this configuration the configuration would include without limitation the appropriate thermal protection, and electronic signal transmission for the analysis of geological fluids. These and other features and advantages of the present invention will be more readily understood by those skilled in the art from a reading of the following detailed description.

In instances, the device may be incorporated into a test kit and method to greatly enhance the use and utility of the kit. Exemplary kits include the Hanby Test Kit, recognized by the U.S. Dept. of Commerce in its "Rapid Commercialization Initiative" Program in 1997 when the Hanby methodology was selected as one of the "Ten Best Environmental Developments in the United States". Development of a prototype read-out device for the Hanby Test Kits in that configuration was accomplished, wherein the device was laboratory and field tested by the EPA and the U.S. Army Corps of Engineers Cold Regions Research and Engineering Laboratory. See, for example the website http://www.crrel.usace.army.mil for two (2) technical reports: ERDC/CR-REL TR-007 and TR-00-20 for evaluations of the Hanby kits and H.E.L.P.MATE 2000 instrument.)

The present disclosure is based on the generation of robust, transient chromophores generated by sigma ($\sigma$) and pi ($\pi$) electrons that engage in bond formation during Friedel-Crafts reactions. These chromophores resonate with frequencies in the near ultraviolet (UV) and visible (Vis) portions of the electromagnetic spectrum. The UV/Vis spectrum of light may be generated, for example, by a tungsten/halogen energy source. The analytical spectral data produced by the present disclosure is based on U.S. Pat. No. 4,992,379, by the present inventor, incorporated herein entirely for all purposes. Further, the present disclosure incorporates the addition of a read-out spectrometric device to display and interpret the chromophoric signals produced by the F-C reactions.

Without limitation by theory, the precise and accurate quantitative and qualitative chemical analysis by this chemical reaction spectrometric (CRS) method may be primarily dependent on the stoichiometric relationship of the FC-reactive components. Secondarily, the bulk amount and anhydrous state of the catalyst has a direct relationship on the quantitative determination in this method. The encapsulation of the catalyst in a permeable polymer tape represents a modification of this technology. Encapsulation of the catalysts in the polymer provides two modifications to the Friedel-Crafts reactions on which this CRS method is based. The polymer is hydrophobic and oleophilic, thus providing the functions of protecting the Lewis acid catalyst from water in the samples. Additionally, the polymer encapsulation of the catalyst allows controlled diffusion of the FC-reactive components of the sample into the catalyst. These significant modifications of the invention provide the chemical and spectral specificity enabling precise chemical quantitative and qualitative analysis.

With reference to FIG. 1, there is illustrated a device 100 for the extraction, chemical-reaction (colorimetric), and spectrometric analysis according to one embodiment of the present disclosure. The device 100 comprises a housing 110. Within in the housing there is a sample extraction chamber (SEC) 120 with a sample access 122 and a sample extraction valve 124. The sample extraction chamber 120 is fluidly connected to the dual-channel syringe 130. Further, the dual-channel syringe 130 is in fluid communication with a solvent reservoir 132 and an extract/catalysts reaction chamber (ECRC) 134. The reaction chamber 134 drains to a waste storage 136. A catalyst tape drum 140 drives a catalyst tape 142 by a motorized means through the reaction chamber 134. Further, a probe 150, comprising a tungsten/halogen light source 152, a spectrometer 154, and electronics compartment 256 are positioned within the housing 110.

Referring to FIG. 2, there is illustrated the probe 150 shown in FIG. 1. The probe 150 comprises a tungsten/halogen light source 152 and a spectrometer 154. The spectrometer 154 comprises a detector 255, such as a charge-coupled device (CCD) and/or a linear array thereof. Further, the spectrometer 154 comprises a diffraction grating 256. In further instances, the catalyst tape 142, comprising individual, separate catalyst packets 243 in a linear arrangement, is configured to pass through the spectrometer 154, under the light source 152 and adjacent the detector 255.

Referring to FIG. 3, there is illustrated the dual channel syringe 130 of the device 100 shown previously in FIG. 1. In configurations, the syringe 130 comprises a solvent extract channel 231 and a solvent channel 232, with associated pistons 231A and 232B respectively. Solvent extract channel 231 comprises a solvent inlet valve 233 and an extract/catalyst reaction chamber (ECRC) valve 235. The solvent extract valve 124 is in fluid communication with the solvent extract channel 231 of the syringe 130. The solvent extract channel 231 is in fluid communication with the extract chamber 120 via the solvent inlet valve 233 and the ECRC 134 via the ECRC valve 235. The solvent channel 232 is in fluid communication with the solvent reservoir 132 via the solvent valve 234. In instances the ECRC valve 235 drains the syringe 130 to the waste storage 136.

In operation the device 110 generates F-C reactions by introducing a sample, including soil, water, or formation fluid via the sample access 122 into the sample extraction chamber 120 using the dual channel syringe 130. The syringe 130 is equipped with valves 136 that regulate the flow of solvent, such as $CCl_4$, from the solvent reservoir 132 into the syringe 130 and, subsequently, into the Extract/Catalyst Reaction Chamber (ECRC) 134. The catalyst tape 142 is fed into the ECRC 134 by the motorized catalyst tape storage drum 140. After a precise time and extraction temperature, which determine the diffusion of the solvent extract into the polyethylene-enclosed catalyst, the resultant chromophoric signal is read by the spectrometer 154. The chromographic signal is digitized into a data signal, for example via a charge-coupled device (CCD). The data signal is electrically transmitted to a computer or other microprocessor-based read-out device. In instances, the data signal is transmitted to a computer via a standard USB connection from the electronic module (not shown) or similar connection.

Referring now to FIG. 4 there is illustrated a method 500 for chromographic analysis according to an exemplary embodiment of the present disclosure. Without limitation, the method 500 comprises introducing the sample 510, injecting a solvent 520, transitioning the sample 530, introducing the catalyst 540, activating the probe 550, and draining the reacted sample 560. In some embodiments, the method further comprises flushing the apparatus 570.

Referring now to FIG. 1 and FIG. 4, the method 500 for chromographic analysis comprises introducing the sample 510 to the device disclosed hereinabove. In instances, the liquid or solid samples are introduced (510) into the sample extraction chamber, 120 via the Sample access 122. Next, injecting a solvent 520 comprises withdrawal of the dual channel syringe 130. This motion causes a small aliquot of the extraction solvent, such as $CCl_4$ from the solvent reservoir 132 to inject into the sample extraction chamber 120. Further, sample transitioning 530 comprises depression of the syringe 130 and simultaneous pressing of the SEC manual valve 124 such that the aliquot of the solvent, such as $CCl_4$, is injected by the left-hand channel (e.g. 231A shown in FIG. 4) of the syringe 130 from the solvent extraction chamber 120 into the extract/catalyst reaction chamber (ECRC) 134. Catalyst introducing 540 comprises the electronic activation of the motorized catalyst tape storage disc drum 140 such that one segment or packet (e.g. 243 shown in FIG. 2) of the catalyst tape 142 is advanced, thereby positioning a catalyst packet (e.g. 243 shown in FIG. 2) under the probe 150, such as a tungsten/halogen light source 152. Further, activating the probe 550 comprises the electronic activation of the tungsten/halogen light source 152, activating the charge-coupled device (CCD) 255 of the spectrometer 154, and in certain instances, sending a digital signal to a computer via a USB port. Reaction draining 560 comprises manual depression of the ECRC drain valve 137, which drains the extract into the extract waste storage reservoir 136. Optionally, flushing 570 of the analytical stream channels and components, when required, is conducted following these steps without introducing a sample. Either prior to, or after flushing 570 permits obtaining a spectrometric blank as needed.

Generally, the aforementioned device is a device for on-site analysis of soil, water, or geological fluids, which provides a method for performing sample extraction, catalytic presentation, and spectrometric signal production as exemplified in the accompanying drawings and comprising the steps: introducing a soil, water, or geological formation fluid into an analytical device, which provides a method of extracting the said sample(s) with an alkyl halide extracting solvent; delivering a precise volume of the said alkyl halide solvent into the device such that a stoichiometric relationship is established with the sample; extracting the said sample in a chamber in the device using the said extracting solvent; delivering the sample extract into a catalyst reaction chamber; introducing a polymer-encapsulated Lewis acid catalyst into the said extracting chamber in a controlled temperature for a controlled time such that the ensuing Friedel-Crafts reaction caused by the catalyst, which is contacted by the solvent-extracted sample, to generate specific chromophores, which quantitatively and qualitatively identify the sample chemically; illuminating the chromophoric signals produced from the chromophores using a tungsten/halogen probe; reading the spectral signals generated by the sample using a CCD-based spectrometer; transmitting the digital signal via a USB port for transmission to a computer.

There a dual-channeled syringe apparatus to withdraw an alkyl halide solvent from a storage reservoir for subsequent introduction into an extraction chamber for extracting a soil, water, or geological formation fluid sample. The dual channel syringe, having a valving arrangement such that the alkyl halide solvent can be transmitted from one channel of the dual-channel syringe into an extraction chamber, thence transmitted to a diffusion/reaction chamber, thence to a spectrometer viewing module, and then to a waste reservoir.

The embodiment described hereinabove is designed as a small-sized device such that it can be easily transported to the field and utilized manually by one person for soil or water analysis for petroleum contamination. Conversely, this small device can be fully automated with appropriate electronic operation of syringe and valving, and utilized with appropriate thermal and vibration insulation as a downhole wireline device for oil exploration purposes (geological formation fluid analysis).

The method described herein is a method of encapsulating a Lewis acid catalyst in a polyethylene tape such that the said tape can be introduced in a time and temperature controlled manner such that specific Friedel-Crafts reactions occur, which generate chromophoric products that provide spectrally definitive signals to precisely identify and quantify the analyte substance. Further, the catalyst can be maintained in an anhydrous state so that it remains active to catalyze Friedel-Crafts reactions. A method of encapsulating a Lewis acid catalyst in a polymer such that diffusion of Friedel-Crafts reactive liquids occurs into the polymer in a precisely controlled time and quantity so that the reaction occurs in a repeatable manner. Also, the method includes controlled presentation of catalyst-enclosed polymer capsules such that they are illuminated by a tungsten/halogen lamp.

The spectrometric signal of the disclosed method is generated by Friedel-Crafts products to be transmitted through a polymer tape in a time and temperature controlled environment such that the signal can be dispersed through a diffraction grating and transmitted to a linear array charge-coupled device for electronic transmission of the digitized signal to a microprocessor device. Further, the polymer tape, which contains encapsulated Lewis acid catalyst packets is maintained in an anhydrous condition and coiled on a feed drum to be sequentially introduced into a reaction chamber for subsequent exposure to Friedel-Crafts reactants.

In the method a soil, water, or formation fluid sample is extracted with an alkyl halide extractant. An especially preferred extractant solvent is carbon tetrachloride. The extract solution is then caused to undergo Friedel-Crafts (FC) reactions by exposure to a Lewis acid catalyst. An especially preferred Lewis acid catalyst is anhydrous Aluminum Chloride. The present invention describes apparatus that can accept the sample(s), the extraction solvent, a means for introducing the sample(s) and solvent into an extraction chamber, a means for presenting a precise amount of the catalyst to the extracted sample solution, a tungsten/halogen source, and a charge-coupled-device (CCD) spectrometer for the detection of the signal generated by the FC-produced chromophores.

Many modifications and variations, particularly in regard to automated or remote actuation, as specifically mentioned in the embodied device and method may be made without departing substantially from the concept of the present invention. Accordingly, it should be clearly understood that the form of the invention described herein is exemplary only, and is not intended as a limitation on the scope thereof.

I claim for patent:

1. A spectrometric analysis system comprising:
    a sample extraction chamber disposed in a housing for providing a sample extract;
    a reaction chamber disposed in the housing for contacting the sample extract with a catalyst to generate chromophoric signals produced by Friedel-Crafts reactions; and
    a spectrometer comprising diffraction grating coupled to a charge-coupled device, wherein the spectrometer is disposed in the housing configured to read the chromophoric signals in the near ultraviolet and visible portions of the electromagnetic spectrum in response to dispersing the chromophoric signals through the diffraction grating of the spectrometer.

2. The system of claim 1, further comprising a light source for illuminating the chromophoric signals in the near ultraviolet and visible portions of the electromagnetic spectrum.

3. The system of claim 1, wherein the charge-coupled device is configured to digitize the chromophoric signal into a data signal.

4. The system of claim 1, wherein the catalyst comprises a catalyst tape including a plurality of separate catalyst packets disposed linearly along the catalyst tape.

5. The system of claim 4, wherein a catalyst disposed in each catalyst packet is encapsulated in a hydrophobic and oleophilic polymer.

6. A spectrometric analysis system comprising:
    a sample extraction chamber configured to receive a sample of geological fluids, and wherein the sample extraction chamber is in fluid communication with a valve for regulating a flow of a solvent into the sample extraction chamber for producing a sample extract from the sample of geological fluids;
    a catalyst tape including a plurality of separate catalyst packets disposed linearly along the catalyst tape;
    a reaction chamber for contacting the sample extract with at least one of the catalyst packets of the catalyst tape to generate chromophoric signals produced by Friedel-Crafts reactions;
    a motorized catalyst tape drum configured to displace the catalyst tape through the reaction chamber;
    a spectrometer configured to read the chromophoric signals; and
    a downhole tool to contain the sample extraction chamber, the valve, the reaction chamber, and the spectrometer, and to receive the sample of geological fluids.

7. The system of claim 6, wherein the spectrometer is configured to read the chromophoric signals in the near ultraviolet and visible portions of the electromagnetic spectrum.

8. The system of claim 6, further comprising a light source for illuminating the chromophoric signals in the near ultraviolet and visible portions of the electromagnetic spectrum.

9. The system of claim 6, wherein the spectrometer comprises a charge-coupled device.

10. The system of claim 9, wherein the charge-coupled device is configured to digitize the chromophoric signal into a data signal.

11. The system of claim 6, wherein the spectrometer is configured to transmit the digital signal to the surface of a wellbore from the downhole tool.

12. The system of claim 6, wherein a catalyst disposed in each catalyst packet is encapsulated in a hydrophobic and oleophilic polymer.

13. A spectrometric analysis system comprising:
a sample extraction chamber disposed in a housing for providing a sample extract;
a reaction chamber disposed in the housing for contacting the sample extract with a catalyst to generate chromophoric signals produced by Friedel-Crafts reactions; and
a spectrometer comprising diffraction grating coupled to a charge-coupled device, wherein the spectrometer is disposed in the housing configured to read the chromophoric signals in the near ultraviolet and visible portions of the electromagnetic spectrum in response to dispersing the chromophoric signals through the diffraction grating of the spectrometer;
wherein the spectrometer is configured to identify the sample extract chemically in response to reading the chromophoric signals.

14. The system of claim 13, wherein the spectrometer is configured to quantitatively and qualitatively identify the sample extract chemically in response to reading the chromophoric signals.

15. The system of claim 13, wherein the spectrometer is configured to read the chromophoric signals in the near ultraviolet and visible portions of the electromagnetic spectrum.

16. The system of claim 13, further comprising a downhole tool to contain the sample extraction chamber, the reaction chamber, and the spectrometer, and to receive geological fluids.

17. The system of claim 13, further comprising a light source for illuminating the chromophoric signals in the near ultraviolet and visible portions of the electromagnetic spectrum.

* * * * *